United States Patent [19]

Dante et al.

[11] Patent Number: 5,365,596
[45] Date of Patent: Nov. 15, 1994

[54] METHODS AND APPARATUS FOR AUTOMATIC IMAGE INSPECTION OF CONTINUOUSLY MOVING OBJECTS

[75] Inventors: Henry M. Dante, Midlothian; David A. Lowitz, Richmond, both of Va.

[73] Assignee: Philip Morris Incorporated, New York, N.Y.

[21] Appl. No.: 992,139

[22] Filed: Dec. 17, 1992

[51] Int. Cl.⁵ .................. G06K 9/00; G06K 9/68; H04N 7/18; G01N 21/00
[52] U.S. Cl. .................................. 382/8; 382/34; 356/237; 348/125
[58] Field of Search ............ 382/8, 1, 14, 30, 33, 382/34; 358/106, 101; 356/237, 430; 250/572

[56] References Cited

U.S. PATENT DOCUMENTS

| | | | |
|---|---|---|---|
| 3,835,332 | 9/1974 | Bridges | 250/563 |
| 4,021,778 | 5/1977 | Ueda et al. | 340/146.3 |
| 4,259,661 | 3/1981 | Todd | 340/146.3 |
| 4,345,312 | 8/1982 | Yasuye et al. | 382/8 |
| 4,581,762 | 9/1986 | Lapidus et al. | 382/8 |
| 4,701,961 | 10/1987 | Hongo | 382/34 |
| 4,776,023 | 10/1988 | Hamada et al. | 382/34 |
| 4,828,156 | 5/1989 | Whiteley et al. | 226/1 |
| 4,866,288 | 9/1989 | Weber | 250/572 |
| 4,891,528 | 1/1990 | Kuecker et al. | 250/548 |
| 4,893,346 | 1/1990 | Bishop | 382/8 |
| 4,924,086 | 5/1990 | Weber | 250/235 |
| 4,952,062 | 8/1990 | Bean, III et al. | 356/430 |
| 4,974,261 | 11/1990 | Nakahara et al. | 382/22 |
| 4,975,971 | 12/1990 | Ohnishi | 382/8 |
| 4,975,972 | 12/1990 | Bose et al. | 382/8 |
| 5,046,111 | 9/1991 | Cox et al. | 382/8 |
| 5,073,952 | 12/1991 | Watanabe | 382/8 |
| 5,129,009 | 7/1992 | Lebeau | 382/8 |
| 5,165,101 | 11/1992 | Cox et al. | 382/8 |

OTHER PUBLICATIONS

Gonzalez et al, Digital Image Processing, Addison Wesley 1992, pp. 544, 556.

*Primary Examiner*—Joseph Mancuso
*Assistant Examiner*—David Fox
*Attorney, Agent, or Firm*—Kevin B. Osborne; James E. Schardt; Charles E. B. Glenn

[57] ABSTRACT

The acceptability of images is determined by comparing each image to a template image which may be an average of several images which are known to be acceptable. The amount by which the image deviates from the template image is used as a measure of the acceptability of the image. Portions of the image at or near edges in the images may be automatically excluded from this test. Another test which includes the edge portions excluded from the first test may be performed to ensure that all portions of the image are inspected. For example, this other test may include ensuring that the correct number of edge pixels are present in the image as a whole.

14 Claims, 10 Drawing Sheets

METHODS AND APPARATUS FOR AUTOMATIC IMAGE INSPECTION OF CONTINUOUSLY MOVING OBJECTS

BACKGROUND OF THE INVENTION

This invention relates to image inspection systems, and more particularly to such systems which are especially suited to high speed inspection of repetitively occurring images and in which it is important to monitor the full grey scale integrity of the images.

Modern high speed printing and/or other product production equipment is capable of producing products at very high speeds. As just one example, cigarette pack blanks may be printed on continuous web presses at speeds of the order of 1000 feet per minute. Because each pack blank is approximately six inches long parallel to the length of the web, each line of pack blanks is coming off the press at the rate of approximately 2000 blanks per minute. (Several parallel lines of blanks (e.g., eight or nine) may be printed across the web.) Accordingly, if each pack blank in a line is treated as an image, the press is producing on the order of 2000 images per minute in each line. Despite the high speed at which such images are being produced, it would be highly desirable to be able to effect complete inspection of all the images. This preferably means inspecting all parts of all of the images, including the full grey scale information for as much of the images as is possible. (As used herein, grey scale means that each pixel in a digitized image is represented by a multidigit binary value or the equivalent thereof.)

Inspection systems are known which inspect only selected portions of images, and/or which discard much of the grey scale information in the images in order to reduce the computational burden. However, systems which inspect only parts of the images miss defects occurring elsewhere in the images. Furthermore, systems which discard available grey scale information may not be able to detect with sufficient promptness gradual fading and/or discoloration of the images.

Another disadvantage of the known systems which inspect only portions of the images and/or which make use of only portions of the information coming from the images is that these known systems tend to require set-up by relatively highly skilled operators who must devote substantial amounts of time to the set-up task. For example, if less than all of each image is to be inspected, the operator must make informed judgments as to the portions of the image which it is most important to inspect, as well as what the criteria for acceptance or rejection in each area will be. Moreover, this complex set-up task must be repeated each time different images are to be inspected.

In view of the foregoing, it is an object of this invention to provide image inspection systems which are capable of substantially complete inspection of images produced at very high speeds.

It is a more particular object of this invention to provide high speed image inspection systems which are capable of full grey scale inspection of at least portions of the images being inspected.

It is still another object of this invention to provide high speed image inspection systems which require relatively little operator time and skill to set them up for an image inspection procedure.

SUMMARY OF THE INVENTION

These and other objects of the invention are accomplished in accordance with the principles of the invention by providing high speed image inspection systems which form a grey scale template image from several representative images of known acceptability. The operator of the system is only required to determine whether these few images (and possibly a further few images mentioned below) are acceptable. If the images to be inspected have substantial numbers of "edges" (i.e., abrupt changes in image intensity such as are typically associated with lettering or other well-defined line work) which are subject to minor but acceptable variation in location in the field of view of the image capturing apparatus, it may also be desirable to have the system compute a mask which can be used to exclude such edge areas from some of the image analysis. In this way the expected and acceptable variations in edges do not cause the system to improperly reject acceptable images. Such a mask is preferably computed from several acceptable images (which may be either the same images used to produce the above-described template image or additional images identified by the operator of the system as acceptable). Each of these images is processed to highlight the edges in the image in a binary representation, and all of the binary images are then combined by a logical OR operation. The result is a mask which can be used to identify all areas in subsequently received images which can be expected to contain edges.

When the template image and (optionally) the mask have been computed, the system is ready to begin actual image inspection. Each image is compared to the template image (e.g., by subtracting the grey scale image from the grey scale template image). The resulting data is preferably binarized to highlight those pixels at which the image being inspected differs from the template image by more than a predetermined amount. If more than a predetermined number of pixels are thus highlighted, the image may be identified as defective. If a mask image has been computed as described above, that mask image may be used at any convenient time to exclude from the foregoing image inspection operation those pixels which have been found to be at or near edges in the image. If this is done, then it is desirable to also carry out a further image inspection operation as follows to make sure that the image (including the masked region) contains approximately the expected number of edges. An edge detection procedure is applied to the image being inspected. The resulting edge detected image is binarized to isolate the edges, and the number of pixels thus identified as being associated with edges is counted. This pixel count must fall within an expected range or the image is identified as being unacceptable because it has too many or too few edges.

Further features of the invention, its nature and various advantages will be more apparent from the accompanying drawings and the following detailed description of the preferred embodiments.

DETAILED DESCRIPTION OF THE PREFERRED EMBODIMENTS

Although the present invention is equally applicable to many other image inspection tasks such as the inspection of the appearance of discrete products (e.g., food, beverage, or other similar packages moving along a packaging line), the invention will be fully understood from the following explanation of its application to inspection of images printed one after another on a continuously moving paper or paperboard web.

Figure 1:
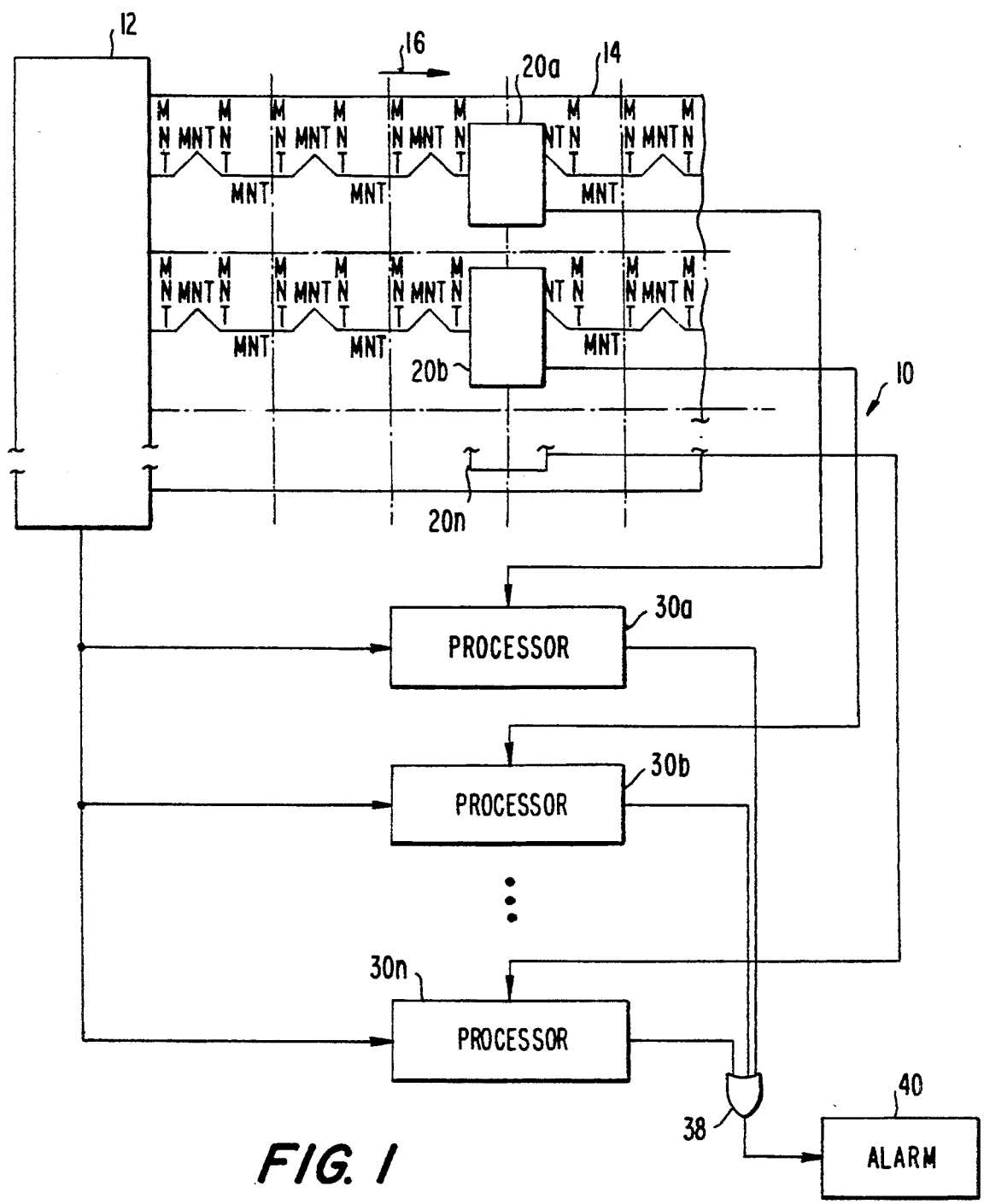
FIG. 1 is a simplified, partial plan view, partly in schematic block diagram form, of illustrative image inspection apparatus constructed in accordance with the principles of this invention.
Figure 4:
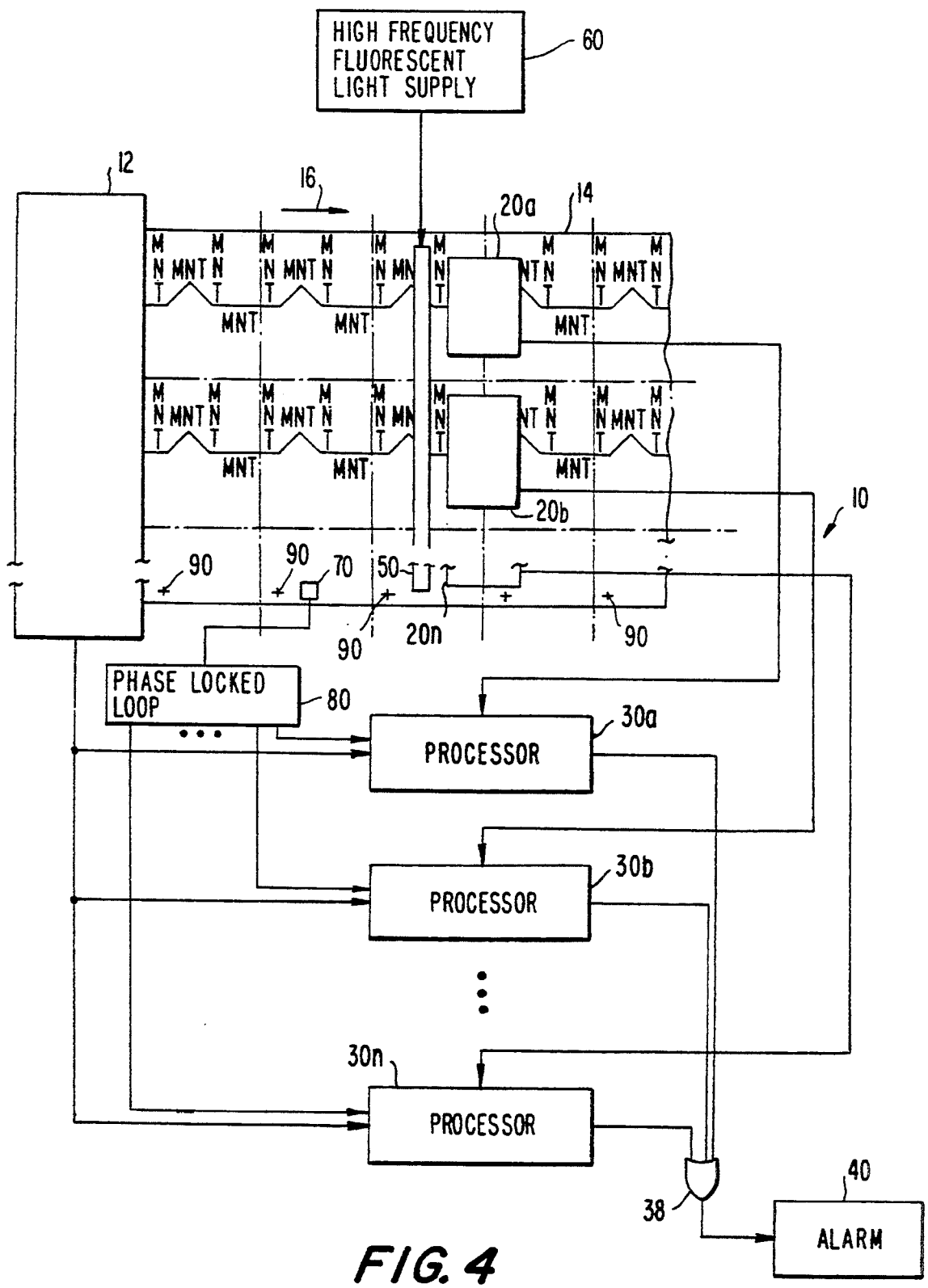
FIG. 4 is a view similar to FIG. 1 showing alternative illustrative image inspection apparatus constructed in accordance with the principles of this invention. The image inspection steps of FIGS. 2 and 3 can also be carried out in the apparatus of FIG. 4.

As shown in FIG. 1, illustrative image inspection apparatus 10 constructed in accordance with this invention is set up to inspect images printed by press 12 on continuously moving paper or paperboard web 14. (FIG. 4 is similar to FIG. 1 but shows several possible modifications which are discussed below.) In the embodiment shown in FIG. 1 press 12 is printing cigarette pack images on web 14 which exits from the press moving to the right as viewed in FIG. 1. Press 12 prints these images in several rows parallel to the axis 16 of motion of the web. For example, although only a few representative rows are shown in FIG. 1, eight or nine rows may be printed across a web which is of the order of 36 or 38 inches wide. Chain dotted lines parallel to axis 16 are used in FIG. 1 to show the approximate boundaries between adjacent rows. Other chain dotted lines perpendicular to axis 16 are used to show the approximate boundaries between adjacent images in each row. After printing as described above and inspection as described below, web 14 may be cut approximately where shown by the chain dotted lines to produce individual cigarette pack blanks. For example, web 14 may first be slit along the chain dotted lines which are parallel to axis 16 to produce individual strips of images. Each of these strips may then be cut transversely across to produce individual blanks. Each blank is subsequently folded around a bundle of cigarettes to produce a finished cigarette pack (e.g., the familiar hinge lid cigarette box).

Although any repeating portion of the material printed on web 14 can be treated as the image to be inspected, for convenience herein it will be assumed that the material printed for each cigarette pack blank is the image to be inspected.

Although the images to be inspected may vary greatly from one inspection task to another, and although the images may be made up of a wide variety of text, graphic, and/or other visually perceptible information, the simplified images shown in FIG. 1 are illustrative of the types of images which it may be desired to inspect. For example, these images include text (i.e., the letters MNT printed in various orientations and representative of brand name and/or other textual information that may need to appear on the finished cigarette packs), and ornamental line work (i.e., the line running across each image generally parallel to axis 16 and representing graphical information such as lines, areas printed in different colors, and other designs, graphical information, and the like). It is generally important to ensure that all of the desired image information is present, that the intensity and colors of all of this information are correct, and that there are no extraneous marks, smears, or other defects in the images. It is especially advantageous catch image defects as they come off press 12 so that prompt steps can be taken to rectify printing problems before large amounts of web stock are wasted. It is also desirable to inspect package images before those images are used to package any contents so that good contents are not wasted by being packaged in defective packaging. The foregoing considerations are especially important when one takes into account the speeds at which modern packaging equipment produces finished product packages. For example, press 12 may print web 14 at the rate of 800 to 1000 feet per minute. This means producing approximately 1600 to 2000 cigarette blanks per minute in each row of blanks parallel to axis 16.

The image inspection apparatus of this invention basically includes one or more cameras or camera-like devices 20 for capturing successive images to be inspected, one or more processors (e.g., conventional programmable digital computers) 30 for processing the image information from cameras 20 and for producing an output indication when an image is found to be defective, and an alarm device 40 for alerting the operator of the system and/or initiating other appropriate action (e.g., automatically stopping press 12) when defective images have been detected. Any of a wide variety of image capturing techniques may be used. For example, as shown in FIG. 1, each of cameras 20a-20n may be aligned with a respective one of the rows of images printed by press 12 so that each camera produces image information for the images in the associated row. Each of processors 30a-30n receives the output signal from a respective one of cameras 20a-20n, and all of processors 30 are synchronized to the operation of press 12 by a synchronizing output signal from the press (e.g., a signal which is produced at frequent intervals by press 12 or a shaft encoder associated with press 12 and which indicates where in its operating cycle the press is). This synchronizing signal will be synchronized to the production of images by the press. Accordingly, each of processors 30 uses this synchronizing signal to determine when to "grab" an image from the associated camera 20 so that each successive image thus grabbed is like all the other images grabbed by that processor (e.g., each successive image is the image of a successive cigarette pack blank area in the associated row of blank images).

As noted above, the above-described image capturing technique is just one example of many that can be used. For example, another way of synchronizing the grabbing of images is shown in FIG. 4 and involves having press 12 periodically print a characteristic mark 90 on web 14 in a predetermined relationship to the pack images. A detector 70 is provided to synchronize image grabbing based on detecting this special mark. As an alternative to detecting a special mark with a dedicated detector, processors 30 can synchronize themselves by looking for a predetermined characteristic of the images being inspected. For example, processors 30 can be set up to look for a particular line transverse to axis 16 in the images, and to time the grabbing of successive images so that this line always occurs at the same relative position in the successive images. Image grabbing can be effected or aided by strobing the illumination of web 14 opposite cameras 20 when it is desired to grab an image. Various kinds of cameras 20 (e.g., full frame, line scan, or time delay integration cameras) can be used as desired.

There are some advantages to using line scan cameras or time delay integration (TDI) line scan cameras for imaging objects like a printed web which presents a continuous image to the inspection system. Unlike the normal area scan cameras where the image is grabbed as a two-dimensional array, the line scan camera consists of only a single line of pixels and outputs one line of the image. When used with a moving object, successive outputs of the line scan camera can be assembled together to get a two-dimensional image. To do this, the rate of line outputs from the camera must be synchronized with the rate of web motion. This can be accomplished by using a shaft encoder coupled to the running web and using the output of the encoder to trigger the line scan camera. The resolution of the picture can then be controlled by controlling the number of pulses per unit length of the web. For example, for 10 mil pixel resolution, the camera should output 100 lines of data for 1 inch of web. This can be done by using a proper shaft encoder with appropriate electronics to control the number of pulses.

In situations like web inspection, with web speeds of 800 to 1000 ft/min., it is advantageous to use TDI line scan cameras (e.g., those available from Dalsa, Inc. of Waterloo, Ontario, Canada) for image grabbing. The TDI camera is an array camera with the data from different lines in the array summed up and the output given in the form of a single line. Since the data is summed up from different lines, the TDI camera needs substantially less light than a line scan camera. The line rate of the TDI camera, which is also equal to the data shift rate along the lines inside the TDI camera, can be controlled by a shaft encoder in a manner similar to the ordinary line scan camera. One other important consideration when using the TDI camera is that the moving object and the data shifting in the camera have to be synchronized, so that the data summed in the lines pertains to the same line in the object.

Whether using a line scan camera or a TDI camera, special considerations have to be given to the way in which the web is illuminated so as to be imaged. This is because the normal 60 Hz supply cannot be used directly to illuminate the web as it will introduce variations in light intensity at the supply frequency. These variations will manifest themselves as supply frequency interference. Consequently, either a DC supply source or a high frequency fluorescent supply source (e.g., one from Mercron of Richardson, Tex.) has to be used. FIG. 4 shows the use of such a high frequency fluorescent light supply 60 with a fluorescent light 50.

It has been mentioned that one way of synchronizing the line scan or TDI camera with web motion is by using a shaft encoder. Another way, which is presently preferred, is to use a phase locked loop 80 with a sensor 70 as shown in FIG. 4. This requires fiducial marks 90 on the web for synchronizing purposes. However, there are typically such marks on webs used for packing materials, and these fiducial marks typically occur at fixed locations for every blank as indicated at 90. Even if such marks do not exist, it is an easy task to incorporate one such fiducial mark by including it in the Gravure process. The output of the phase locked loop is an inteqral multiple of the input pulses once the system locks onto the input frequency. The multiplication factor is controlled by using an adjustable counter in the loop feedback path. Additional details regarding phase locked loops can be obtained from the book by D. H. Wolaver entitled *Phase-Locked Loop Circuit Design*, Prentice-Hall, N.J., 1991. Once the distance between fiducial marks 90 and the desired pixel resolution are known, the multiplier factor for the loop can be easily calculated. For example, for a label length of 6 inches with one fiducial mark for every label, and a resolution of 10 mils, the multiplier factor is 600. If desired, the phase locked loop can be built with presettable counters which are set during the initial set-up procedure of the apparatus.

An example of equipment suitable for use as processors 30 is the MaxVideo20 pipelined image processing board available from Datacube, Inc., of Peabody, Mass. The MaxVideo20 is an extremely fast image grabbing and processing hardware which has the necessary computing power to implement the inspection system described here. The MaxVideo20 can be plugged into a VME computer system like a SUN3 or SUN4 computer available from Sun Microsystems, Inc., of Mountain View, Calif. or a Maxbox System available from Data Cube, Inc., of Peabody, Mass., which works as the host for the image processing hardware. The MaxVideo20 can input images from conventional area scan, line scan, or TDI cameras at speeds of up to 20 MHz. It also includes arithmetic and pipeline processors which perform image processing operations in pipelined configurations at a sustained rate of 20 MHz. It can also output images on a monitor with resolutions up to 1024×1024 pixels. It is a flexible system and can be programmed to perform a variety of image processing functions.

Figure 2A:
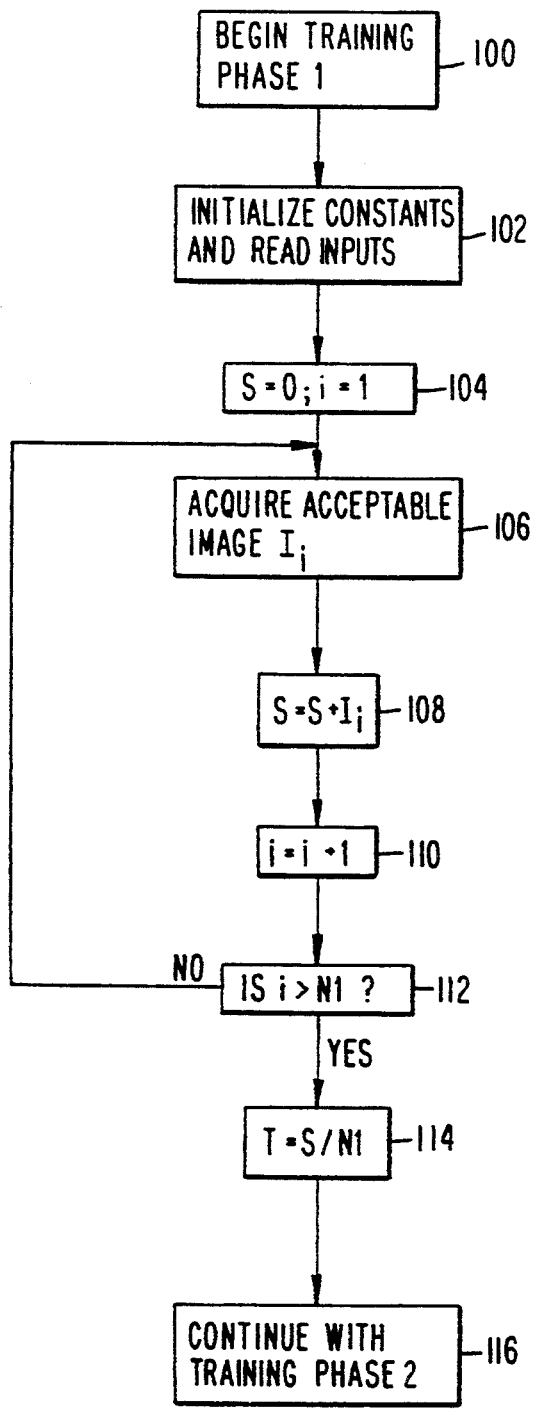
FIGS. 2a-2d (sometimes referred to collectively as FIG. 2) are a flow chart of illustrative image inspection steps which can be carried out in the apparatus of FIG. 1.
Figure 2B:
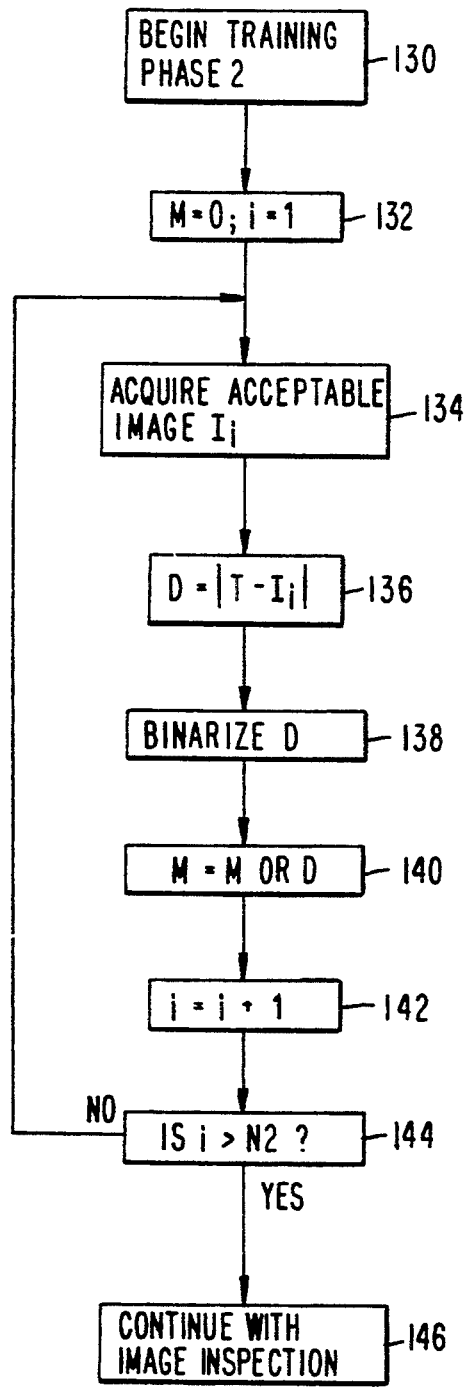
Figure 2C:
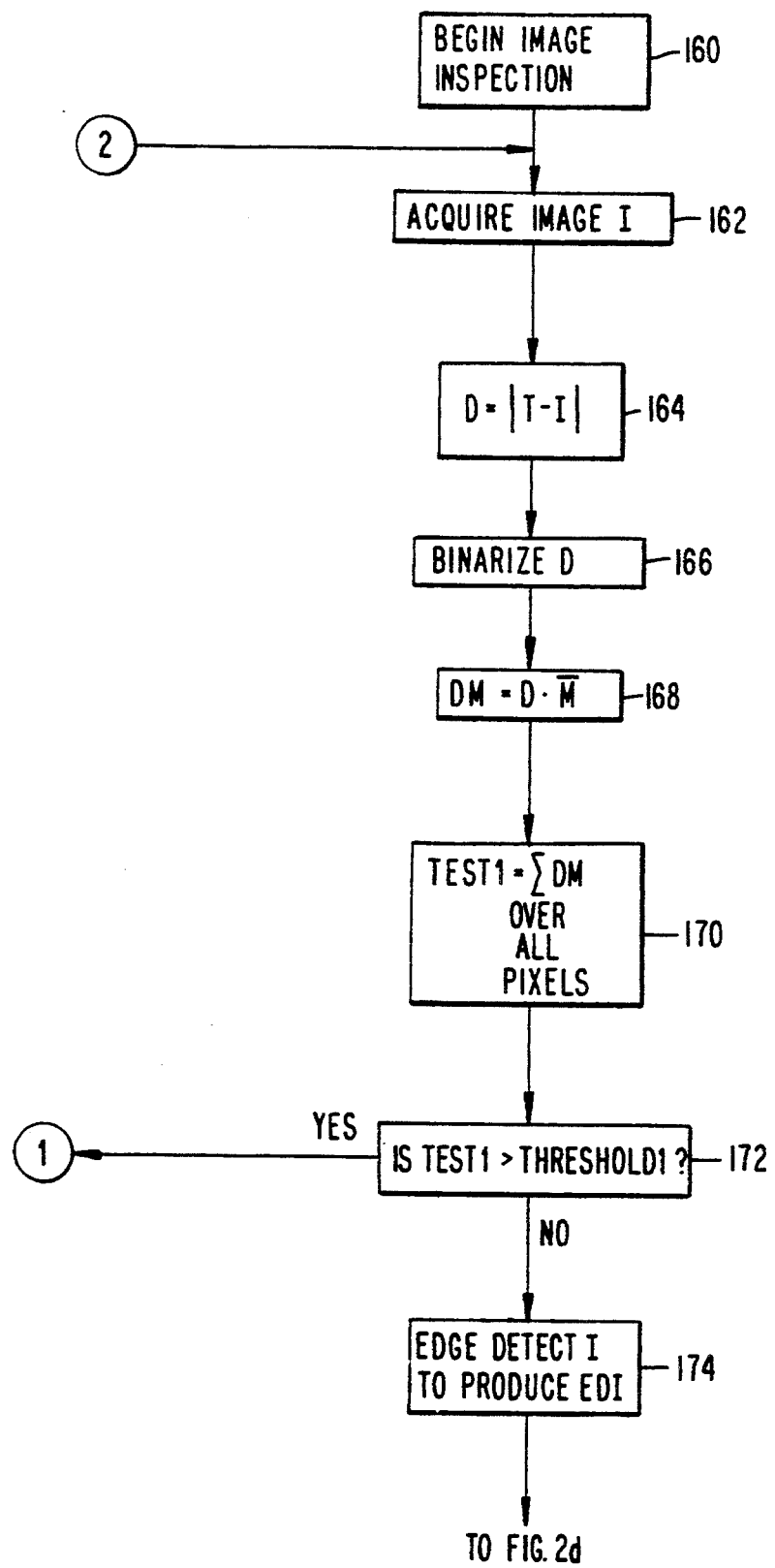
Figure 2D:
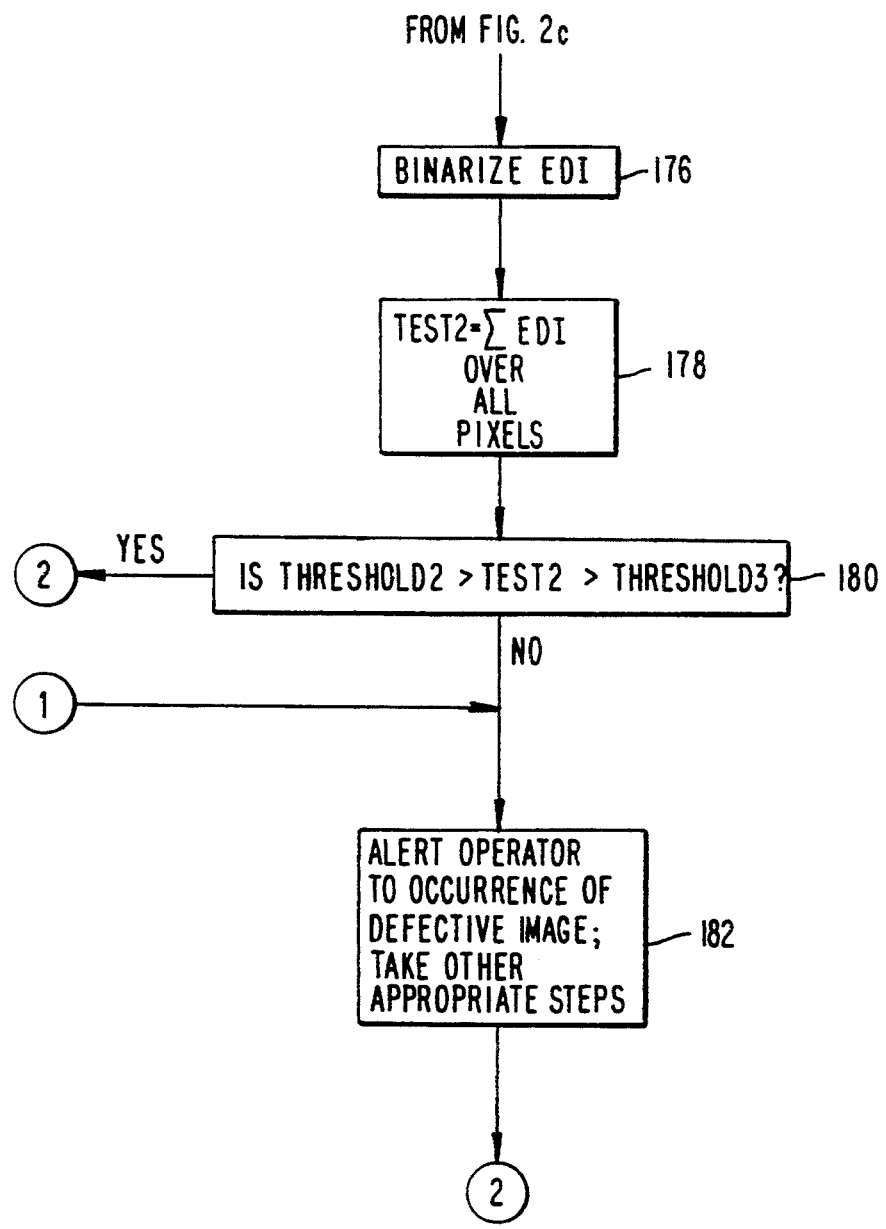

In addition to including the imaging hardware needed to grab and digitize successive images from the associated camera 20, each processor 30 in FIG. 1 or FIG. 4 performs the steps needed to actually inspect each image. An illustrative embodiment of a suitable sequence of image inspection steps in accordance with this invention is shown in FIG. 2. This sequence of steps includes a first training phase (FIG. 2a) in which the system generates a so-called template image T for use in subsequent actual image inspection (FIGS. 2c and 2d). In addition, FIG. 2b shows an optional second training phase (which can be performed after the first training phase and before actual image inspection). In this second training phase a mask can be generated for use in segregating two different types of image areas for different treatment during actual image inspection. The training phase or phases are provided to enable the system to gather for itself substantially all of the detailed image information needed during actual image inspection to determine whether or not the images being inspected are acceptable. This greatly facilitates the task of setting up the system for each new inspection operation. The time and skill level required from the operator to set the system up are thereby greatly reduced.

Turning now to a detailed consideration of FIG. 2, the training phase or phases (FIGS. 2a and 2b) are performed when setting the system up to perform an inspection task. The first training phase begins with step 100. In step 102 the system is initialized in the way which is conventional for programmed digital processors by supplying initial values and parameters needed by the system to begin to operate. These values may be input to processors 30 from a conventional keyboard and/or touch screen (not shown).

In step 104 all of the pixel values in a so-called sum image S are initialized to 0, and an index variable i is initialized to 1. In step 106 the system acquires a first image. The images acquired in step 106 are digitized, full grey scale images. Although step 106 can be performed in other ways such as by using image specifications or an image prototype, a preferred way to perform step 106 is simply to operate press 12 to print images and have elements 20 and 30 capture the required image from the resulting web 14 as described above. This first image should be one which is known to be acceptable. This can be determined by the operator of the system (e.g., by visual inspection of a display of the grabbed image on a conventional display device (not shown) driven by processors 30).

In step 108 the image from step 106 is added on a pixel by pixel basis to the sum image S to produce a new sum image.

In step 110 i is incremented by 1, and in step 112 i is compared to a limit value N1 which is the number of images to be used in the determination of the template image T. For example, N1 may be a relatively small number like 8 or a somewhat larger number like 100. If i is not yet greater than N1, steps 106–112 are repeated for another acceptable image. When the desired number of acceptable images have been processed in the corresponding number of repetitions of steps 106–112, the final performance of step 112 causes control to pass to step 114.

In step 114 the value of each pixel in the sum image is divided by N1 to produce a grey scale template image T. Accordingly, each pixel value in T is the average of the values of the corresponding pixels in N1 training images of known acceptability. Template image T is therefore an average acceptable image. The first training phase ends with step 116.

If the images to be inspected contain well defined edges to a substantial extent, then it may be advantageous to next perform training phase 2 (FIG. 2b) to identify those portions of the image which contain such edges. Edges are regions of abrupt transition in grey scale value (i.e., due to abrupt changes in image intensity and/or color). For example, lettering is almost always defined by edges along the boundaries of the line work which forms the lettering. Because of slight variations in the locations of such edges from image to image (due, for example, to such factors as unavoidable vibration or shifting in the location of web 14, minor variations in the timing of the image grabbing operation, etc.), pixel values at or near edges may vary considerably from image to image, although all of the images are perfectly acceptable. It would therefore be undesirable to base the acceptance or rejection of an image on stringent requirements regarding pixel values at or near edges. In such cases, training phase 2 (FIG. 2b) can be performed to identify edge regions in the image so that those edge regions can be excluded when comparing images to be inspected using template image T.

Training phase 2 begins with step 130, and in step 132 all pixels in a mask image M are initialized to 0 and an index value i is initialized to 1.

In step 134 an acceptable image is acquired exactly as described above in connection with step 106. (Indeed, if the data for the training images acquired during the first training phase has been saved, this data can be reused during training phase 2 to avoid having to gather any more training image data.)

In step 136 the absolute value of the difference between T and the image from step 134 is computed on a pixel by pixel basis to produce a difference image D.

In step 138 difference image D is binarized using a binarizing threshold which highlights (i.e., sets equal to 1) each pixel in D which deviates from the corresponding pixel in T by more than a predetermined grey scale amount. All other pixels (which do not significantly deviate from T) are set equal to 0. It is generally sufficient to use a single binarization threshold value for all pixels.

In step 140 D is combined on a pixel by pixel basis with mask image M using a logical OR operation to produce new mask image values.

In step 142 i is incremented by 1, and in step 144 i is compared to a predetermined limit value N2. Until i exceeds N2 for the first time, steps 134–144 are repeated for successive phase 2 training images. N2 may be a number like N1. Accordingly, mask image M gradually becomes a map of all pixels in acceptable images which may vary significantly from corresponding template image T pixels because of slight but acceptable variations in the locations of image edges. As soon as i exceeds N2 for the first time, control passes to step 146 which concludes training phase 2 and allows actual image inspection to begin.

As shown in FIG. 2c, actual image inspection begins with step 160. In step 162 an image I to be inspected is acquired as described above in connection with FIG. 1. This is a full grey scale image.

In step 164 the absolute value of the difference between the template image T and the image I from step 162 is computed on a pixel by pixel basis to produce difference image D.

In step 166 difference image D from step 164 is binarized in a manner analogous to above-described step 138. Accordingly, in step 138 a binarizing threshold is used to highlight (by setting equal to 1) those pixels in I which vary by more than a predetermined grey scale amount from the corresponding pixel values in T. All other pixels in binarized difference image D are set equal to 0. Again, it is generally sufficient to use a single binarization threshold for all pixels, although different binarization thresholds can be used for different portions of the image (e.g., differently colored portions of the image) if desired.

In step 168 the logical AND of the binarized difference image from step 166 and the complement of the mask image M from the final performance of step 140 is formed on a pixel by pixel basis to produce masked difference image DM. This operation effectively eliminates from DM all pixels which are at or near edges in acceptable images. Accordingly DM will have pixel values of 1 only for pixels which are not at or near edges in acceptable images and which differ significantly from the corresponding pixel value in T.

In step 170 the values of all pixels in DM are added together. This provides a count of the pixels which deviate significantly from T and which are not at or near edges. The value of this count is TEST1.

In step 172 TEST1 is compared to a predetermined value THRESHOLD1, which may be any desired threshold value selected by the operator of the system during initialization step 102. If TEST1 is greater than THRESHOLD1, the image being inspected has been determined to be unacceptable and control passes from step 172 to 182. Otherwise the process of inspecting the current image may continue with step 174.

Because the use of mask image M effectively excludes from image inspection steps 164–172 pixels which are at or near edges, it is desirable to have some other steps (e.g., steps 174–180) which include inspection of those portions of the image. Moreover, even if mask image M is not used, it may still be desirable to apply an additional test of image acceptability such as steps 174–180 after the image successfully completes steps 164–172.

In step 174 the grey scale image data from step 162 is subjected to an edge detection operation to produce an edge detected image EDI. In EDI pixels at edges have relatively high grey scale values, while all other pixels have relatively low grey scale values. For detecting the edges in an image, any of the conventional edge detection operators (e.g., the so-called Roberts, Sobel, or Laplacian edge detection operators) can be used. In the particularly preferred embodiments, however, the modified morphological edge detection operation described below is used. This edge detection technique gives very sharp edges and the overall image inspection process works better with this technique.

At the heart of the morphological edge detection technique are simple grey scale morphological operations erosion and/or dilation. The dilation operation gives a dilated grey scale image ID in which each pixel value is the maximum of the original image pixel values in the neighborhood of the pixel. In particular, for a three-pixel by three-pixel neighborhood dilation, each pixel ID(i,j) in the dilated image is given by:

$$ID(i,j) = \max[I(i-1, j-1), I(i-1, j),$$
$$I(i-1, j+1), I(i, j-1), I(i,j),$$
$$I(i, j+1), I(i+1, j-1),$$
$$I(i+1, j), I(i+1, j+1)]$$

where I is the original image.

Similarly, the erosion operation gives an eroded grey scale image IE in which each pixel value is the minimum of the original image pixel values in the neighborhood of the pixel. In particular, for a three-pixel by three-pixel neighborhood erosion, each pixel IE(i,j) in the eroded image is given by:

$$IE(i,j) = \min[I(i-1, j-1), I(i-1, j),$$
$$I(i-1, j+1), I(i, j-1), I(i,j),$$
$$I(i, j+1), I(i+1, j-1),$$
$$I(i+1, j), I(i+1, j+1)]$$

The edge detected image EDI can be obtained from the dilated and/or eroded images in any of several ways. For example, the edge detected image can be the difference between the dilated and original images (which gives outer edges). Alternatively, the edge detected image can be the difference between the original and eroded images (which gives inner edges). As still another alternative, the edge detected image can be the difference between the dilated and eroded images (which gives both the outer and inner edges in an image).

Continuing now with the discussion of FIG. 2, in step 176 EDI is binarized so that pixels at edges have pixel values of 1, while all other pixels have pixel values of 0.

In step 178 all of the pixel values in EDI are added together to produce the value TEST2. TEST2 is therefore a count of the number of pixels associated with edges in I.

In step 180 a test is performed to determine whether or not TEST2 is within acceptable limits given by predetermined values THRESHOLD2 and THRESHOLD3, which may be any desired threshold values selected by the operator of the system during initialization step 102. If TEST2 is between THRESHOLD2 and THRESHOLD3, image I has been found to have approximately the correct number of pixels in its edge regions. This may mean, for example, that all text and other well defined line work is present with the correct intensity. Control therefore passes from step 180 back to step 162, where inspection of the next image begins. On the other hand, if TEST2 is too low, this may mean that certain text is absent, too faint, obscured by other matter which has become too intense, or that other normally edge-rich features are similarly defective. Or if TEST2 is too high, it may mean that unwanted additional edges (e.g., spots, streaks, smears, blobs, etc.) are present in the image. In either case in which TEST2 is outside the acceptable limits, control passes from step 180 to step 182.

Step 182 is performed whenever an image is found to be unacceptable (i.e., either as a result of the test performed in step 172 or the test performed in step 180). In step 182 the operator is alerted to the detection of an unacceptable image. With reference to FIG. 1, whenever any of processors 30 performs step 182, that processor produces an output signal which is applied to OR gate 38. Accordingly, alarm device 40 is activated whenever any of processors 30 detects an unacceptable image. In addition, other steps appropriate to the detection of an unacceptable image may be taken. For example, press 12 may be stopped, the unacceptable image may be displayed to help the operator of the system identify and correct the problem, and/or the portion of web 14 containing the unacceptable image may be sprayed with some marker, or have a tag attached to the web edge, to help the operator quickly find the defective image and/or to help apparatus subsequently involved in the use of the web reject bad material. Unless the press is stopped as part of step 182, image inspection may continue after each performance of step 182 by passing control from step 182 back to step 162.

Figure 3A:
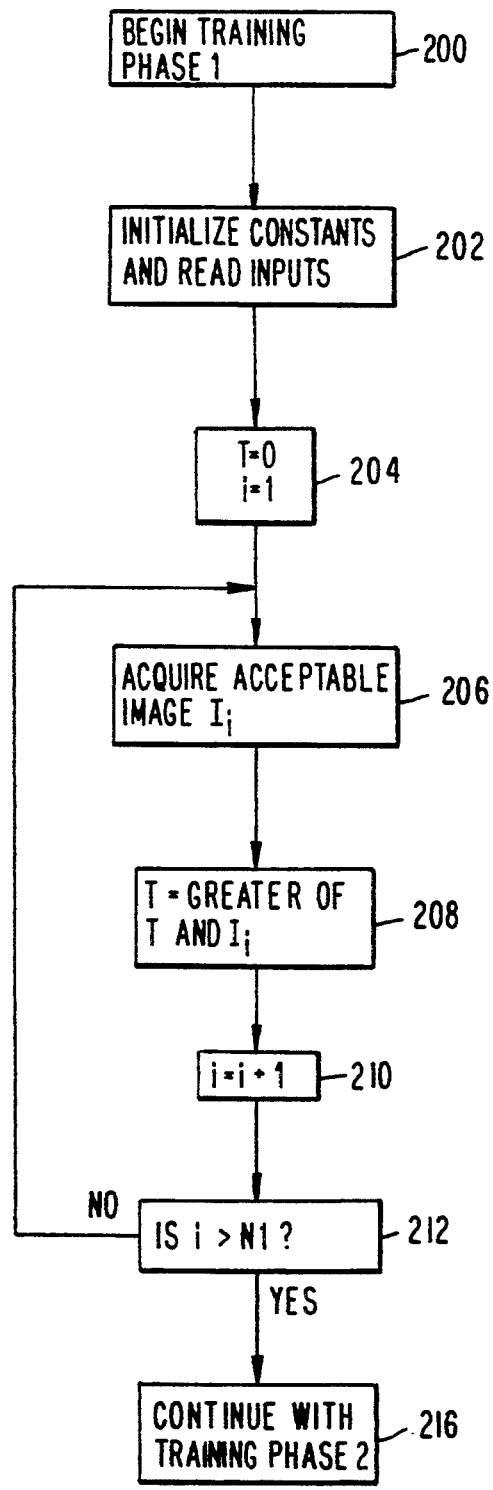
FIGS. 3a-3d (sometimes referred to collectively as FIG. 3) are a flow chart of alternative image inspection steps which can be carried out in the apparatus of FIG. 1.
Figure 3B:
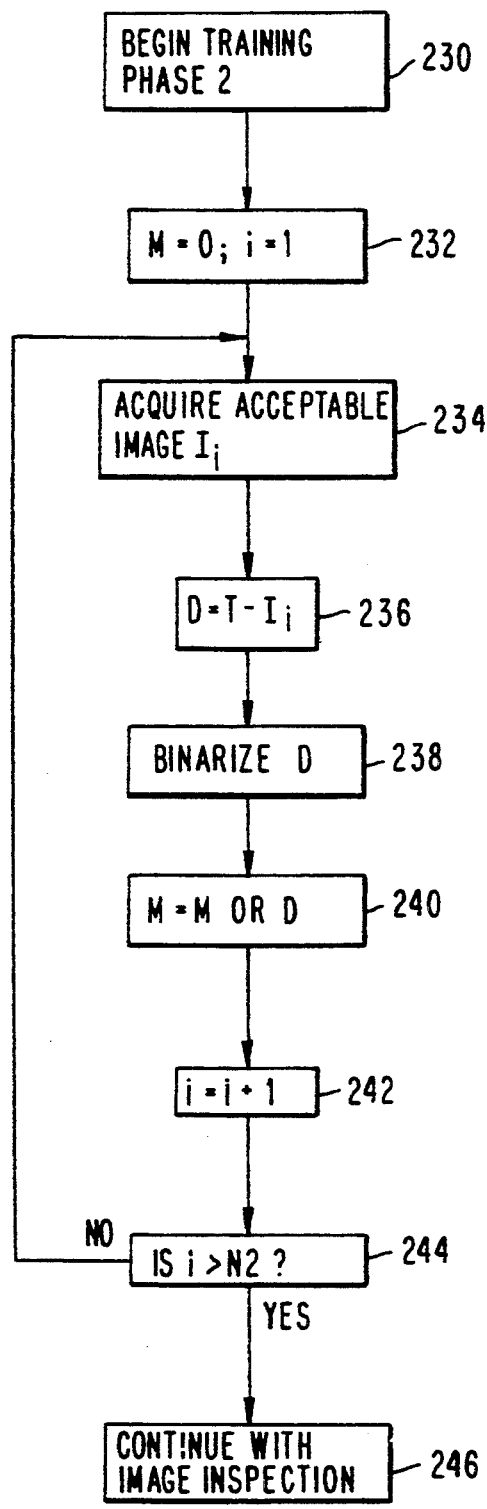
Figure 3C:
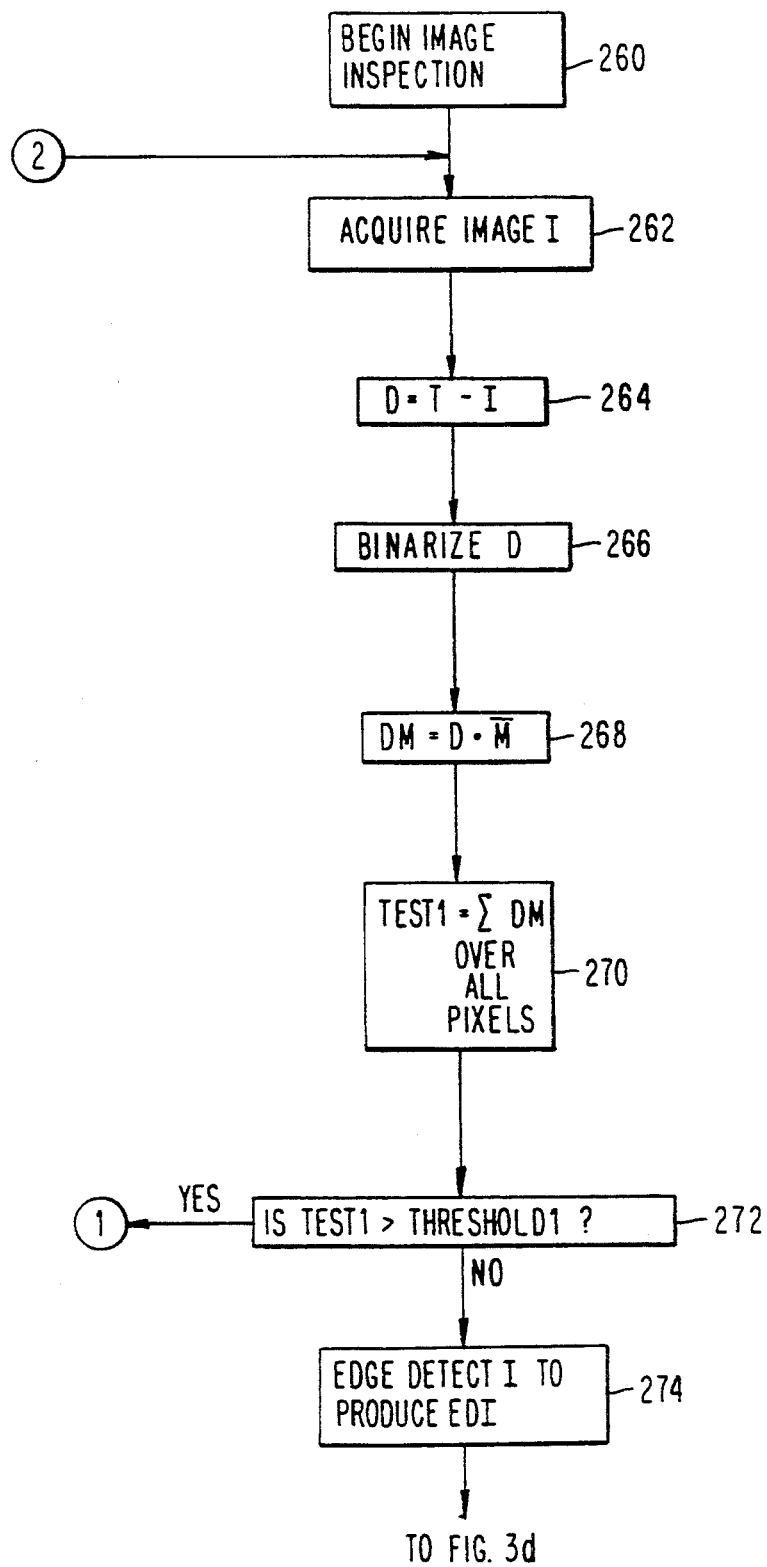
Figure 3D:
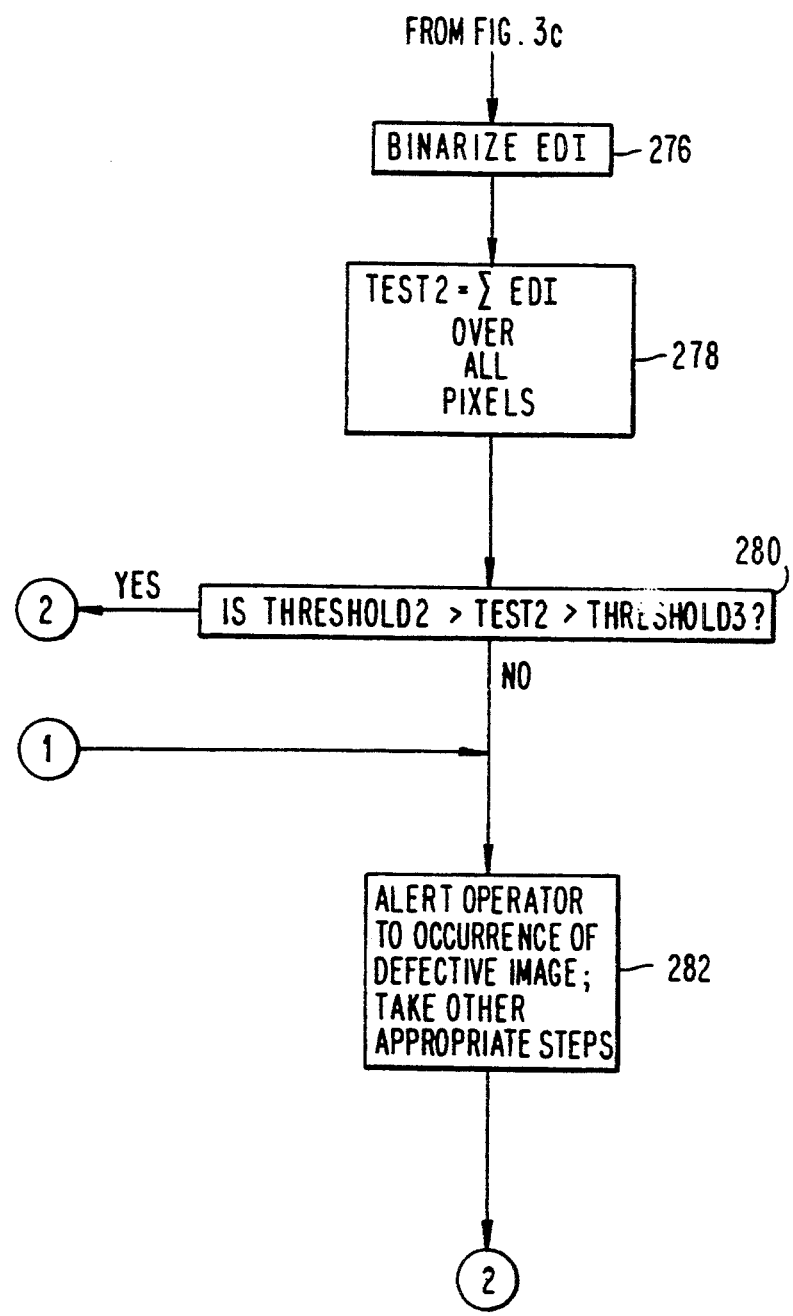

It will be understood that the foregoing is merely illustrative of the principles of the invention and that various modifications can be made by those skilled in the art without departing from the scope and spirit of the invention. For example, FIG. 3 shows an alternative embodiment in which the template image values are chosen differently to avoid the need to take absolute values in the steps analogous to steps 136 and 164 in FIG. 2. Elimination of the absolute value operations allows the image inspection process to be performed more rapidly. In FIG. 3a steps 200 and 202 are respectively similar to steps 100 and 102 in FIG. 2a. In step 204 each pixel value in template image T is initialized to the smallest possible value (e.g., 0), and i is initialized to 1. Step 206 is similar to step 106 in FIG. 2a. In step 208 each pixel value in T is set equal to the greater of the previous value of that pixel value in T or the corresponding pixel value in the current training image I. Steps 210, 212, and 216 are then respectively similar to steps 110, 112, and 116 in FIG. 2a. Accordingly, at the end of the first training phase each template image value is equal to the largest value encountered for that pixel in any of the training images. To account for any variation not represented by the training images, the pixel value in T may be increased by a small positive value (e.g., by adding 5 or 10 to each of the pixels). This makes it unnecessary to take absolute values in either step 236 in FIG. 3b or step 264 in FIG. 3c. This is because using the highest permissible value for each pixel in the template image makes all acceptable difference values in steps 236 and 264 relatively small positive numbers. Any relatively large positive difference number and any negative difference number (which in conventional two's complement representation looks like an even larger positive number) is unacceptable. Therefore this alternative eliminates the need to take absolute values in steps 236 and 264, and still allows the use of only a single binarization threshold value in each of steps 238 and 266. Except as discussed above, steps 230–282 in FIGS. 3b–3d may be respectively similar to steps 130–182 in FIGS. 2b–2d.

Many other modifications within the scope of this invention are also possible. For example, although binarization step 166 is preferred because it reduces step 170 to the relatively simple operation of counting pixels whose value is 1, step 166 could be eliminated and a true summation of grey scale difference values could be performed in step 170. If training phase 2 is not used and no mask image M is available, step 168 can be eliminated and DM in step 170 replaced by D (either binarized if step 166 is included or unbinarized if step 166 is omitted). As still another possible modification, training phase 1 could be substantially eliminated by generating template image T from a single prototype image or from image specifications to which erosion and/or dilation operations have been applied in a manner analogous to the way in which such operations are used in commonly assigned, co-pending application Ser. No. 742,323, filed Aug. 8, 1991, which is hereby incorporated by reference herein.

The invention claimed is:

1. The method of determining whether an image is substantially like a predetermined image which is subject to some minor but acceptable variations, said method comprising the steps of:
    (1) forming a template image which is representative of said predetermined image and said minor but acceptable variations by performing the steps of:
        (a) identifying a plurality of training images, each of which is substantially like said image, and at least some of which includes at least some of said minor but acceptable variations from said image;
        (b) representing each of a plurality of portions of each of said training images by a pixel value, each of said portions of each of said training images respectively corresponding to an associated one of said portions of said template image; and
        (c) for each portion of said template image, using as the template image pixel value the largest of the pixel values for the associated portion in said training images;
    (2) representing each of a plurality of portions of said template image by a pixel value;
    (3) representing each of a plurality of portions of said image of a pixel value, each of said portions of said image respectively corresponding to an associated one of said portions of said template image;
    (4) for each of said portions of said image, determining the difference between the pixel value of that portion of said image and the pixel value for the associated template image portion;
    (5) cumulating said differences for at least some of said portions of said image to produce a cumulative difference value;
    (6) comparing said cumulative difference value to a predetermined threshold value; and
    (7) identifying said image as unlike said predetermined image if said cumulative differences value bears a predetermined relationship to said threshold value.

2. The method defined in claim 1 wherein each of said pixel values of each of said training images is a grey scale value.

3. The method defined in claim 1, further comprising the steps of
    identifying the portions of said image which are at or near regions of abrupt change in pixel value in the image; and
    excluding said portions of said image which are at or near said regions of abrupt change in pixel value from the portions of said image for which said step of cumulating said differences is performed.

4. The method defined in claim 1, further comprising the steps of
    identifying which of said portions of said image are associated with regions of abrupt change in pixel value in said image;
    counting the number of said portions of said image which are associated with regions of abrupt change in pixel value; and
    identifying said image as unlike said predetermined image if said number is not within a predetermined range.

5. The method defined in claim 3 wherein said step of identifying the portions of said image which are at or near regions of abrupt change in pixel value comprises the steps of:
    identifying a plurality of training images, each of which is substantially like said image, and at least some of which include at least some of said minor but acceptable variations from said image;
    representing each of a plurality of portions of each of said training images by a pixel value, each of said portions of each of said training images respectively corresponding to an associated one of said portions of said template image;
    for each portion of each of said training images, determining the deviation between the pixel value for that portion of that training image and the pixel value for the associated template image portion; and
    identifying as portions of said image that are at or near regions of abrupt change in pixel value any portions of any of said training images for which said deviation is greater than a predetermined amount.

6. The method defined in claim 5 wherein said step of identifying as a region of abrupt change in pixel value comprises the steps of:
    binarizing said deviations by assigning a first binary value to all portions of each training image for which said deviation is less than a predetermined amount, and by assigning a second binary value to all portions of each training image for which said difference is greater than said predetermined amount; and identifying as portions of said image that are at or near regions of abrupt change in pixel value any portions of any of said training images which have said second binary value.

7. The method defined in claim 4 wherein said step of identifying which of said portions of said image are associated with edges in said image comprises the step of edge detecting said image.

8. Apparatus for determining whether an image is substantially like a predetermined image which is subject to some minor but acceptable variation, said apparatus comprising:
   (1) means for forming a template image which is representative of said predetermined image and said minor but acceptable variation wherein said means for forming a template image comprises:
      (a) means for identifying a plurality of training images, each of which is substantially like said image, and at least some of which include at least some of said minor but acceptable variations from said image;
      (b) means for representing each of a plurality of portions of each of said training images by a pixel value, each of said portions of each of said training images respectively corresponding to an associated one of said portions of said template image; and
      (c) means for, for each portion of said template image, using as the template image pixel value the largest of the pixel values for the associated portion in said training images;
   (2) means for representing each of a plurality of portions of said template image by a pixel value;
   (3) means for representing each of a plurality of portions of said image by a pixel value, each of said portions of said image respectively corresponding to an associated one of said portions of said template image;
   (4) means for, for each of said portions of said image, determining the difference between the pixel value for that portion of said image and the pixel value for the associated template image portion;
   (5) means for cumulating said differences for at least some of said portions of said image to produce a cumulative difference value;
   (6) means for comparing said cumulative difference value to a predetermined threshold value; and
   (7) means for identifying said image as unlike said predetermined image of said cumulative difference value bears a predetermined relationship to said threshold value.

9. The apparatus defined in claim 8 wherein each of said pixel values of each of said training images is a grey scale value.

10. The apparatus defined in claim 8, further comprising
    means for identifying which of said portions of said image are associated with regions of abrupt change in pixel value in said image;
    means for counting the number of said portions of said image which are associated with regions of abrupt change in pixel value; and
    means for identifying said image as unlike said predetermined image if said number is not within a predetermined range.

11. The apparatus defined in claim 8, further comprising
    means for identifying the portions of said image which are at or near regions of abrupt change in pixel value in the image; and
    means for excluding said portions of said image which are at or near regions of abrupt change in pixel value in the image from the portions of said image on which said means for cumulating said differences operates.

12. The apparatus defined in claim 10 wherein said means for identifying which of said portions of said image are associated with edges in said image comprises means for edge detecting said image.

13. The apparatus defined in claim 11 wherein said means for identifying the portions of said image which are at or near regions of abrupt change in pixel value comprises:
    means for identifying a plurality of training images, each of which is substantially like said image, and at least some of which include at least some of said minor but acceptable variations from said image;
    means for representing each of a plurality of portions of each of said training images by a pixel value, each of said portions of each of said training images respectively corresponding to an associated one of said portions of said template image;
    means for, for each portion of each of said training images, determining the deviation between the pixel value for that portion of that training image and the pixel value for the associated template image portion; and
    means for identifying as portions of said image that are at or near regions of abrupt change in pixel value any portions of any of said training images for which said deviation is greater than a predetermined amount.

14. The apparatus defined in claim 13 wherein said means for identifying as a region of abrupt change in pixel value comprises:
    means for binarizing said deviations by assigning a first binary value to all portions of each training image for which said deviation is less than a predetermined amount, and by assigning a second binary value to all portions of each training image for which said difference is greater than said predetermined amount; and
    means for identifying as portions of said image that are at or near regions of abrupt change in pixel value any portions of any of said training images which have said second binary value.

* * * * *